US008398687B2

(12) United States Patent
Vasta et al.

(10) Patent No.: US 8,398,687 B2
(45) Date of Patent: Mar. 19, 2013

(54) VOLAR PLATE FIXATION DEVICE

(75) Inventors: Paul J. Vasta, McKinney, TX (US); Michael G. Thomas, Van Alstyne, TX (US); David Ruch, Chapel Hill, NC (US); David Nelson, Greenbrae, CA (US); Dwight Bronson, Coppell, TX (US)

(73) Assignee: AMEI Technologies, Inc., Wilmington, DE (US)

( * ) Notice: Subject to any disclaimer, the term of this patent is extended or adjusted under 35 U.S.C. 154(b) by 1027 days.

(21) Appl. No.: 11/567,661

(22) Filed: Dec. 6, 2006

(65) Prior Publication Data

US 2008/0140127 A1    Jun. 12, 2008

(51) Int. Cl.
*A61B 17/80* (2006.01)

(52) U.S. Cl. .................................. 606/284; 606/291
(58) Field of Classification Search .......... 606/280–299, 606/70–71
See application file for complete search history.

(56) References Cited

U.S. PATENT DOCUMENTS

| | | | |
|---|---|---|---|
| 4,565,193 A | 1/1986 | Streli |
| 4,905,679 A | 3/1990 | Morgan |
| 4,955,886 A | 9/1990 | Pawluk |
| 5,006,120 A | 4/1991 | Carter |
| 5,015,248 A | 5/1991 | Burstein et al. |
| 5,085,660 A | 2/1992 | Lin |
| 5,190,544 A | 3/1993 | Chapman et al. |
| 5,197,966 A | 3/1993 | Sommerkamp |
| 5,304,180 A | 4/1994 | Slocum |
| 5,364,398 A | 11/1994 | Chapman et al. |
| 5,429,641 A | 7/1995 | Gotfried |
| 5,586,985 A | 12/1996 | Putnam |
| 5,601,553 A | 2/1997 | Trebing et al. |
| 5,709,682 A | 1/1998 | Medoff |

(Continued)

FOREIGN PATENT DOCUMENTS

| | | |
|---|---|---|
| DE | 4343117 A1 | 6/1995 |
| EP | 1211992 B1 | 1/2004 |

(Continued)

OTHER PUBLICATIONS

International Search Report for PCT/US2007/086450 mailed May 13, 2008.

(Continued)

*Primary Examiner* — Kevin T Truong
*Assistant Examiner* — Matthew Lawson
(74) *Attorney, Agent, or Firm* — Baker & McKenzie LLP (57) ABSTRACT

Disclosed embodiments describe a volar plate generally for use treating distal volar fractures. The volar plate is designed in accordance with anatomical features and is generally Y-shaped, having a wider distal head portion that tapers to a narrower proximal body portion. A plurality of holes in the distal head of the volar plate allow for fixation means to fix the position of bone fragments with respect to the volar plate. The plurality of holes in the distal head basically form two substantially non-linear rows, with the distal row generally curving inward proximally and the proximal row generally curving outward distally such that the fixation means inserted through the holes generally converge. A central cavity may be located in the proximal body of the volar plate to promote bone growth, and mounting screws may border the central cavity on either side to provide secure support. Additionally, K-wire holes may be included which are visually linked to corresponding holes in the distal head.

39 Claims, 5 Drawing Sheets

U.S. PATENT DOCUMENTS

| | | | |
|---|---|---|---|
| 5,709,686 A | 1/1998 | Talos et al. | |
| 5,718,704 A | 2/1998 | Medoff | |
| 5,749,872 A * | 5/1998 | Kyle et al. | 606/66 |
| 5,772,662 A | 6/1998 | Chapman et al. | |
| 5,779,703 A | 7/1998 | Benoist | |
| 5,853,413 A | 12/1998 | Carter | |
| 5,931,839 A | 8/1999 | Medoff | |
| 5,938,664 A | 8/1999 | Winquist et al. | |
| 5,941,878 A | 8/1999 | Medoff | |
| 5,964,763 A | 10/1999 | Incavo et al. | |
| 5,968,047 A | 10/1999 | Reed | |
| 6,030,389 A | 2/2000 | Wagner et al. | |
| 6,077,266 A | 6/2000 | Medoff | |
| 6,096,040 A * | 8/2000 | Esser | 606/280 |
| 6,113,603 A | 9/2000 | Medoff | |
| 6,129,728 A | 10/2000 | Schumacher et al. | |
| 6,129,730 A | 10/2000 | Bono et al. | |
| 6,152,927 A | 11/2000 | Farris | |
| 6,221,073 B1 | 4/2001 | Weiss et al. | |
| D443,060 S | 5/2001 | Benirschke et al. | |
| 6,228,085 B1 | 5/2001 | Theken et al. | |
| 6,283,969 B1 | 9/2001 | Grusin | |
| 6,355,042 B2 | 3/2002 | Winquist et al. | |
| 6,358,250 B1 | 3/2002 | Orbay | |
| 6,364,882 B1 | 4/2002 | Orbay | |
| 6,440,135 B2 | 8/2002 | Orbay | |
| D469,533 S | 1/2003 | Bryant et al. | |
| 6,508,819 B1 | 1/2003 | Orbay | |
| D469,874 S | 2/2003 | Bryant et al. | |
| 6,623,486 B1 | 9/2003 | Weaver | |
| 6,652,530 B2 | 11/2003 | Ip et al. | |
| 6,712,820 B2 | 3/2004 | Orbay | |
| 6,866,665 B2 | 3/2005 | Orbay | |
| 7,128,744 B2 | 10/2006 | Weaver et al. | |
| 7,294,130 B2 * | 11/2007 | Orbay | 606/291 |
| 2001/0011172 A1 | 8/2001 | Orbay et al. | |
| 2002/0013587 A1 | 1/2002 | Winquist | |
| 2002/0032446 A1 | 3/2002 | Orbay | |
| 2002/0143338 A1 | 10/2002 | Orbay et al. | |
| 2002/0156474 A1 | 10/2002 | Wack et al. | |
| 2003/0055429 A1 | 3/2003 | Ip et al. | |
| 2003/0083660 A1 | 5/2003 | Orbay | |
| 2003/0105461 A1 | 6/2003 | Putnam | |
| 2003/0153918 A1 | 8/2003 | Putnam et al. | |
| 2004/0030339 A1 | 2/2004 | Wack et al. | |
| 2004/0059334 A1 | 3/2004 | Weaver et al. | |
| 2004/0102778 A1 * | 5/2004 | Huebner et al. | 606/71 |
| 2004/0167522 A1 * | 8/2004 | Niederberger et al. | 606/69 |
| 2004/0193155 A1 | 9/2004 | Castaneda | |
| 2004/0225291 A1 * | 11/2004 | Schwammberger et al. | 606/71 |
| 2005/0049594 A1 * | 3/2005 | Wack et al. | 606/69 |
| 2005/0065522 A1 * | 3/2005 | Orbay | 606/69 |
| 2005/0065524 A1 * | 3/2005 | Orbay | 606/69 |
| 2005/0080421 A1 | 4/2005 | Weaver et al. | |
| 2005/0085818 A1 * | 4/2005 | Huebner | 606/69 |
| 2005/0182406 A1 * | 8/2005 | Orbay et al. | 606/69 |
| 2005/0234458 A1 * | 10/2005 | Huebner | 606/69 |
| 2005/0240185 A1 * | 10/2005 | Boomer et al. | 606/69 |
| 2005/0240187 A1 * | 10/2005 | Huebner et al. | 606/69 |
| 2006/0089648 A1 * | 4/2006 | Masini | 606/69 |
| 2006/0149250 A1 | 7/2006 | Castaneda et al. | |
| 2006/0161158 A1 | 7/2006 | Orbay | |
| 2006/0217722 A1 * | 9/2006 | Dutoit et al. | 606/69 |
| 2006/0235402 A1 | 10/2006 | Celli et al. | |
| 2006/0235404 A1 | 10/2006 | Orbay | |
| 2006/0259039 A1 * | 11/2006 | Pitkanen et al. | 606/69 |
| 2006/0264947 A1 * | 11/2006 | Orbay et al. | 606/69 |
| 2007/0239163 A1 * | 10/2007 | Strnad et al. | 606/72 |
| 2007/0270853 A1 * | 11/2007 | Leung | 606/69 |
| 2008/0132960 A1 * | 6/2008 | Weaver et al. | 606/308 |

FOREIGN PATENT DOCUMENTS

| | | |
|---|---|---|
| WO | 9426193 | 11/1994 |
| WO | WO9747251 | 12/1997 |
| WO | 2005046494 A1 | 5/2005 |

OTHER PUBLICATIONS

Geissler et al., "Percutaneous and Limited Open Reduction of the Articular Surface of the Distal Radius", Journal of Orthopaedic Trauma, 1991 vol. 5, No. 3, pp. 255-264.

Jupiter et al., "Operative Treatment of Volar Intra-Articular Fractures of the Distal End of the Radius", Journal of Bone and Joint Surgery, Incorporated, vol. 78-A, No. 12, Dec. 1996, pp. 1817-1828.

Peine et al., "Comparison of Three Different Plating Techniques for the Dorsum of the Distal Radius: A Biomechanical Study", The Journal of Hand Surgery, Jan. 2000, vol. 25A, No. 1, pp. 29-33.

Lacroix, et al., "Operative Treatment of Unstable Distal Radial Fractures", The Netherlands Journal of Surgery, 1987, 39(2), pp. 59-64.

Carter et al., "Open Reduction and Internal Fixation of Unstable Distal Radius Fractures with a Low-Profile Plate: A Multicenter Study of 73 Fractures", The Journal of Hand Surgery, Mar. 1998, vol. 23A, No. 2, pp. 300-307.

Keating et al., "Internal Fixation of Volar-Displaced Distal Radial Fracture", The Journal of Bone and Joint Surgery, 1994, vol. 76-B, No. 3, pp. 401-405.

Smith et al., "Open Reduction and Internal Fixation of Volar Lip Fractures of the Distal Radius", J. Orthrop Trauma, 1998, vol. 2, No. 3, pp. 181-187.

Ring et al., "Prospective Multicenter Trial of a Plate for Dorsal Fixation of Distal Radius Fractures", The Journal of Hand Surgery, 1997, vol. 22A, No. 5, pp. 777-784.

Jupiter, J., "Current Concepts Review Fractures of the Distal End of the Radius", The Journal of Bone and Joint Surgery, Mar. 1991, vol. 73-A, No. 3, pp. 461-469.

Kambouroglou et al., "Complications of the AO/ASIF Titanium Distal Radius Plat System (n Plate) in Internal Fixation of the Distal Radius: A Brief Report", The Journal of Hand Surgery, 1998, vol. 23A, No. 4, pp. 737-741.

Laseter et al., "Management of Distal Radius Fractures", Journal of Hand Therapy, Apr.-Jun. 1996, vol. 9, No. 2, pp. 114-128.

Melone, C., "Distal Radius Fracutres: Patterns of Articular Fragmentation", Orthopedic Clinics of North America, Apr. 1993, vol. 24, No. 2, pp. 239-253.

Gesensway et al. "Design and Biomechanics of a Plate for the Distal Radius", The Journal of Hand Surgery, 1995, vol. 20A, No. 6, pp. 1021-1027.

Osada et al., "Comparison of Different Distal Radius Dorsal and Volar Fracture Fixation Plates: A Biomechanical Study", The Journal of Hand Surgery, Jan. 2003, vol. 28A, No. 1, pp. 94-104.

Orbay, J., "The Treatment of Unstable Distal Radius Fractures with Volar Fixation", Hand Surgery, Dec. 2000, vol. 5, No. 2, pp. 103-112.

Orbay et al., "Volar Fixed Angle Plate Fixation for Unstable Distal Radius Fractures in the Elderly Patient", The Journal of Hand Surgery, Jan. 2004, vol. 29A, No. 1, pp. 96-102.

Osada et al., "Biomechanics in Uniaxial Compression of Three Distal Radius Volar Plates", The Journal of Hand Surgery, May 2004, vol. 29A, No. 3, pp. 446-451.

Orbay et al., "Volar Fixation for Dorsally Displaced Fractures of the Distal Radius: A Preliminary Report", The Journal of Hand Surgery, Mar. 2002, vol. 27A, No. 2, pp. 205-215.

Constantine, et al. "Volar Neutralization Plate Fixation of Dorsally Displaced Distal Radius Fractures", Apr. 12, 2004.

Extended European Search Report, Application No. /Patent No. 07854942.5-1526/2099373; PCT/US2007/086450, dated Jun. 19, 2012.

* cited by examiner

VOLAR PLATE FIXATION DEVICE

FIELD OF THE INVENTION

Disclosed embodiments relate generally to fixation of bone fractures to aid in healing, and more specifically to internal fixation devices designed to stabilize wrist fractures of the distal volar radius.

BACKGROUND OF THE INVENTION

While all bone fractures may be serious injuries requiring precise treatment for healing, wrist fractures seem to require extra care; proper alignment and fixation of bone fragments is critical for effective healing of the wrist joint. This point may be illustrated by considering a typical wrist fracture from a fall. Generally a wrist fracture occurs when compression forces on the distal radius cause a break in the bone, with the distal fragment becoming displaced dorsally. Such a fracture often results in multiple bone fragments, each free floating and improperly aligned with respect to the other fragments. Without effective treatment (aligning and fixing the position of the fragments), the bone fragments from the fracture would knit together improperly during the healing process, resulting in possible deformity, loss of range of motion, and/or long-term discomfort. Thus, it is important to properly align the fracture fragments and to fix the bones in place relative to one another so that proper healing may occur.

Conventional methods for treating wrist fractures include casting, external fixation, interosseous wiring, and plating. Each of these techniques have their limitations, however. Casting is a fairly simple, non-invasive external fixation technique, but because it does not provide the precision associated with internal alignment and fixation of individual bone fragments, it is generally too crude to effectively treat complex wrist fractures when used alone. External fixators try to mold fracture fragments into alignment using tension applied across a fracture by the surrounding soft tissue. For wrist fractures with multiple bone fragments, however, external fixators may be unable to effectively position all of the fragments. Interosseous wiring, on the other hand, places a screw into each bone fragment and then uses wiring to brace the fragments in place. While this technique may be effective, it is both difficult and time-consuming to perform. It requires a great deal of skill and precision on the part of the surgeon, since only a complex wire bracing system specifically created for a particular patient's injury can properly stabilize multiple bone fragments.

Plating systems have also been utilized to attempt to stabilize the bone fragments associated with wrist fractures. Conventionally, a metal plate would be mounted to the fractured bones using a set of pins. While this sort of surgical plate system seems to offer advantages over other conventional techniques, it has been in its infancy to date and requires further refinement to provide effective alignment and stabilization of wrist fractures. Accordingly, disclosed embodiments relate to improved volar plate devices that provide a stabilizing framework allowing for proper alignment and fixation of bone fragments during the healing process. Disclosed embodiments take advantage of detailed anatomical analysis of the distal volar radius region, providing an internal fixation device that complements the bones' innate design to effectively align and support the fracture site.

SUMMARY OF THE INVENTION

The volar plate embodiments disclosed herein relate to internal fixation devices designed in accordance with anatomical studies, with the goal of providing an effective stabilization framework for support of the fracture site while allowing adequate range of motion of the injured wrist for effective physical therapy. By using a volar plate rigidly attached to the bone and physically supporting bone fragments in proper alignment, disclosed embodiments provide a support framework that allows physical therapy to begin relatively early. This is important because it allows range of motion and functional use of the injured wrist to be emphasized throughout the treatment regimen, while ensuring that bone fragments are stably held in proper alignment for healing.

The disclosed embodiments generally comprise a volar plate designed for rigid attachment to the bone at the fracture site. The volar plate would typically be positioned on the volar side of the fractured radius bone, and would be held in place using bone screws anchored to the bone. The shape of the present volar plate is designed to mimic and mesh with the bone surface geometry of the volar surface of the distal radius. Thus, the volar plate tends to employ a wider distal head portion that tapers to a narrower proximal body portion. The distal head generally would angle upward away from the generally flat proximal body portion of the volar plate, forming a concave upper surface (as the plate curves upward near the distal end).

The curved upper surface of the volar plate, resulting from the angled attachment of the distal head portion to the proximal body portion, mimics the curvature of the distal volar surface of the radius bone. The volar plate's anatomical shape also allows for screw placement that essentially tracks the articular surface of the distal radius, basically following the subchondral bone contour line. The plate's shape provides anatomical alignment of the plate within the pronator quadratus fossa, allowing bone screws to obtain purchase in the dorsal subchondral bone without danger of protrusion into the joint space.

A complicating factor in designing a volar plate based on anatomical modeling is that studies have shown that the volar surface geometry of the distal radius is not always standard, but varies depending upon the individual. To account for this variance, allowing for more precise fitting of the volar plate during surgical implantation, a crease may score the bottom surface of the corner of the volar plate relating to the radial styloid, allowing the doctor to bend that corner of the distal head portion of the volar plate to adjust the fit based on a particular patient's bone geometry. Accordingly, disclosed embodiments provide for a volar plate designed to interact effectively with the patient's bone structure, thus providing an effective base of support for a wrist fracture. By utilizing an anatomically designed volar plate, the disclosed embodiments reduce the risk of improper plate and screw placement and provide for successful, reproducible outcomes when mounting the volar plate on the bone.

The distal head of the volar plate contains a plurality of holes, through which bone screws, K-wires, sutures, or some other effective fixation means may be inserted to fix bone fragments in place relative to one another and to the distal head of the radius via the volar plate. While the volar plate provides the underlying support, forming a steady base for affixing bone fragments, the fixation means (removably attached to the head of the volar plate, typically by insertion through the plurality of holes in the distal head of the volar plate) actually create the stabilization framework for the fracture. The fixation means (such as bone screws) hold the bone fragments in proper position, allowing effective healing. Bone screws are generally used as the primary fixation means, since the threading along the length of their shafts seems to provide a more secure stabilization framework by obtaining purchase in the bone fragments.

Typically, there would be two rows of holes located on the distal head of the volar plate, and each of the holes would be substantially the same size. The proximal row would have three or more holes, allowing fixation means to be employed through the volar plate. Generally, the disclosed embodiments utilize a substantially non-linear alignment of the holes in the proximal row, with the interior hole(s) distal to the two outside holes. The distal row would also have three or more holes allowing fixation means to be employed through the volar plate. Again, the disclosed embodiments utilize a substantially non-linear alignment of the holes in the distal row in an attempt to more closely match the contours of the articular surface of the distal radius, basically following the subchondral bone contour line in order to provide a stabilization framework that accommodates and interacts synergistically with the patient's actual anatomy. So for example, the interior hole(s) of the distal row would be proximal to the two outer holes.

The orientation of the plurality of holes in the distal head of the volar plate (based on the angle in which the holes penetrate the volar plate and the angle at which threads may be set) determines the orientation of the fixation means (for example, bone screws threadably screwed into the volar plate) projecting out from the bottom surface of the head of the volar plate. When the fixation means are inserted through the holes in the head of the volar plate, the distal row of fixation means would follow a downward angulation similar to the joint surface, allowing the fixation means to reach subchondral bone without entering the joint space, while the proximal row of fixation means would converge on the distal row of fixation means to provide support. By way of example (using bone screws as the fixation means), the screws of the proximal row would extend out between the screws of the distal row. Thus, the screws of the distal and proximal rows would be interleaved, creating an effective stabilization framework for bone fragments. This arrangement also accommodates various length screws which may be necessary for various sizes (depths) of radii across the population.

The volar plate may also contain a central cavity, located generally in the vicinity of the region of the volar plate where the distal head angles away from the proximal body. The central cavity may provide convenient access for the introduction of grafting materials during the treatment regimen. Furthermore, a plurality of mounting screw holes (or some other such means for fixation of the plate onto the bone) are located within the proximal body of the volar plate, allowing the plate to be mounted in place securely on the bone and/or to address more proximal fractures. One or more mounting screw holes are generally located towards the proximal end of the volar plate (and one or more of these mounting screw holes could be configured as an elongated slot, allowing longitudinal adjustment of the volar plate as it is being affixed by the surgeon), while two mounting screw holes would generally be located more distally, with one on either side of the central opening. All of these mounting screw holes allow the volar plate to be firmly fixed in place on the bone, providing a secure base for the stabilization framework. Finally, the volar plate may also include smaller holes for K-wires, allowing temporary fixation of the volar plate in place during the surgical procedure in such a way that the surgeon may correctly position and temporarily fix the volar plate prior to affixing it securely to the bone via bone screws.

So generally, disclosed embodiments provide for a volar plate designed in accordance with the anatomical region of the distal radius, having a wider distal head portion that narrows to a generally flat proximal body, with the head angling up from the plane of the proximal body to form a concave upper surface. The head of the volar plate would generally have two rows of holes, allowing bone screws or some other fixation means to be inserted through the volar plate to fix the position of bone fragments with respect to each other and with respect to the volar plate. The location and angle of the holes would provide for fixation of the fragments in accordance with the anatomical geometry of the distal radius, such that the screws in each row would generally follow a non-linear arc shape, converging in an interleaved manner to provide a secure stabilization framework for the bone fragments. The volar plate may further aid in healing of the fracture by incorporating a central cavity, which allows introduction of grafting and/or bone void filler material. Due to unique design features, disclosed volar plate embodiments offer improved stabilization and support for the healing of bone fractures, while allowing for a range of motion for physical therapy.

BRIEF DESCRIPTION OF THE DRAWINGS

Embodiments are illustrated by way of example in the accompanying figures, in which like reference numbers indicate similar parts, and in which.

DETAILED DESCRIPTION OF EMBODIMENTS

Disclosed embodiments relate to surgically implanted internal fixation devices designed in accordance with anatomical studies. The disclosed embodiments comprise a volar plate designed for rigid attachment to the bone at the fracture site. Generally, the volar plate would be positioned on the volar side of a fractured radial bone, and would be held in place using bone screws anchored into the bone surface.

Additionally, bone screws could be used to fix the position of bone fragments, stabilizing the wrist fracture.

Figures 1, 2:
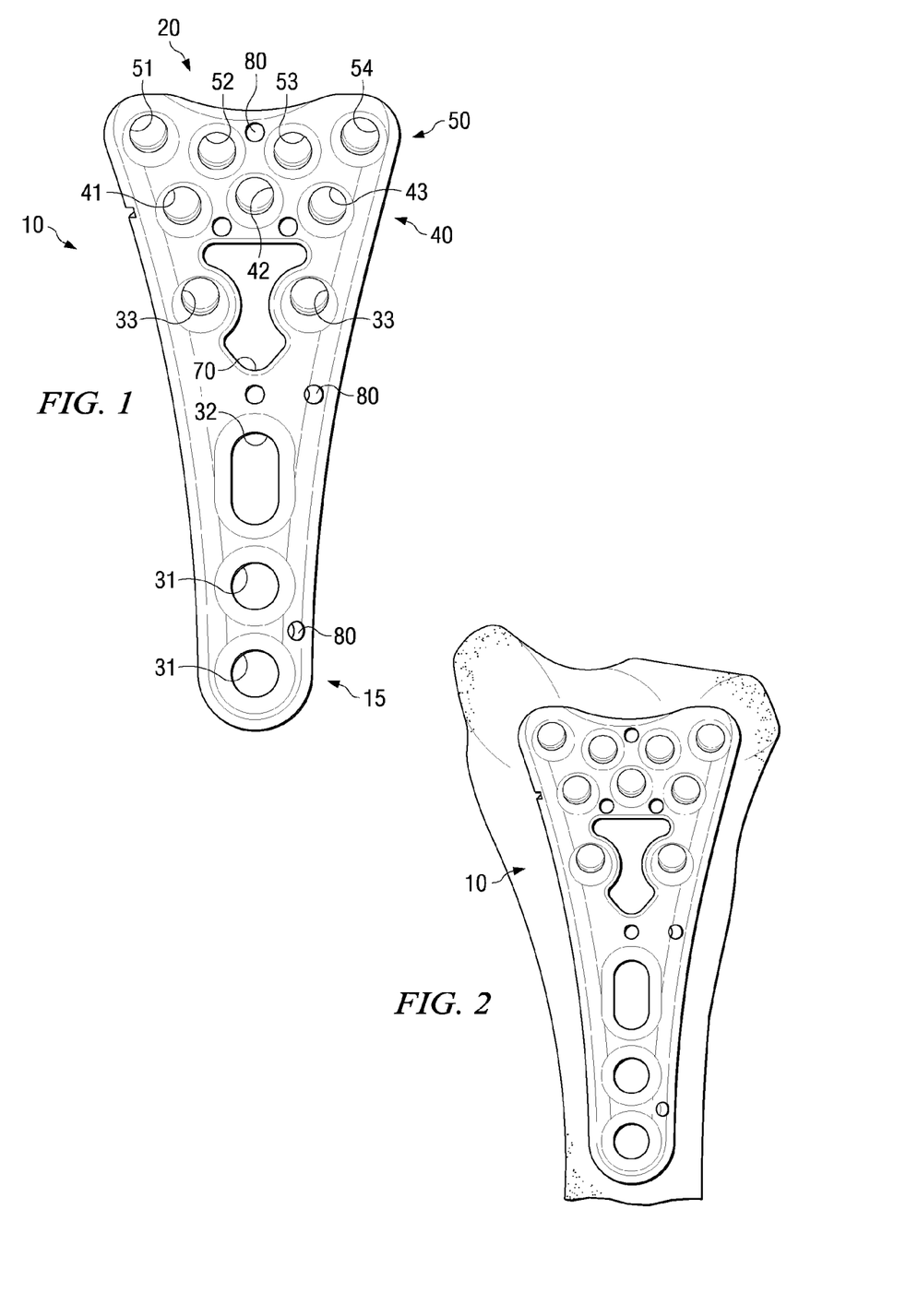
FIG. 1 is a plan view of an embodiment of the volar plate, showing the upper surface of the volar plate.
FIG. 2 is an illustration demonstrating the manner in which the design of a disclosed embodiment of the volar plate incorporates natural anatomical features associated with the distal radius to provide improved fit and function.

FIG. 1 generally demonstrates an embodiment of the volar plate 10, illustrating the basic shape and features generally associated with the present volar plate 10, while FIGS. 3A, 3B, 3C, and 3D further demonstrate the disclosed volar plate showing different views and bone screw placement. The volar plate of FIG. 1 employs a generally Y-shaped plate 10, with a wider distal head portion 20 that tapers to a narrower proximal body portion 15. The distal head 20 angles upward away from the plane of the generally flat proximal body portion 15 of the volar plate, forming a concave upper surface 17. When the volar plate 10 is in place on the bone, the bottom surface 18 (which is opposite the upper surface) of the volar plate 10 would contact the bone. While the volar plate 10 could be constructed of any surgically safe material sufficiently strong and rigid to support bone fragments, the volar plate 10 of FIG. 1 is generally made of medical grade anodized titanium or stainless steel.

The Y-shaped volar plate 10 may vary in size, allowing the surgeon the option to select the volar plate 10 that best fits a particular patient. Typically, the volar plate 10 of the embodiment shown in FIG. 1 might range in width, having a distal head portion 20 from approximately 20 mm to 30 mm across. Likewise, the length of the volar plate 10 might range from approximately 45 mm to 100 mm. Most commonly, volar plates 10 tend to be 50 mm to 65 mm in length. And in the embodiment of FIG. 3C, the angle between the distal head 20 and the proximal body 15 is approximately twenty-five degrees. While specific disclosed embodiments may tend to have dimensions in the ranges discussed above, such dimensions are merely exemplary; a wide range of dimensions may be appropriate for the volar plate 10, and all are intended to be included within the scope of this disclosure.

The shape of the volar plate 10 is designed to mimic and mesh with the bone surface geometry of the distal radius, as illustrated in FIG. 2. The curved upper surface 17 of the volar plate, resulting from the angled attachment of the distal head portion 20 to the proximal body portion 15, mimics the curvature of the articular surface of the radius bone. Likewise, the Y-shape of the plate 10 allows for screw placement that essentially tracks the contours of the articular surface of the distal radius, basically following the subchondral bone contour line. The plate's shape provides anatomical alignment of the volar plate 10 within the pronator quadratus fossa, allowing bone screws to obtain purchase in the dorsal subchondral bone without danger of protrusion into the wrist joint space.

A complicating factor in designing a volar plate 10 based on anatomical modeling is that studies have shown that the volar surface geometry of the distal radius may not be standard, varying depending upon the individual. To account for this variance, allowing for more precise fitting of the volar plate 10 during surgical implantation, a crease 60 (more clearly visible in FIG. 3D) may score the bottom surface 18 of the corner of the distal head 20 of the volar plate 10 relating to the radial styloid, allowing the doctor to more easily bend that corner of the distal head portion 20 of the volar plate 10 to adjust the fit based on a particular patient's bone geometry. Furthermore, the prominence of the lunate facet may be variable, such that alternative embodiments may utilize a volar plate 10 with a curved distal end, with varying degrees of curvature laterally across the distal end of the volar plate, providing a high contour plate designed to align with greater protrusions of the lunate facet or a low contour plate for patients with less curvature along the pronator quadratus line. Accordingly, the embodiment of FIG. 1 provides for a volar plate 10 designed to interact effectively with the patient's bone structure, thus providing a stable base of support for a wrist fracture. By utilizing an anatomically designed volar plate 10, the risk of improper plate and screw placement is reduced, providing for successful, reproducible outcomes when mounting the volar plate 10 on the bone.

Figure 3A:
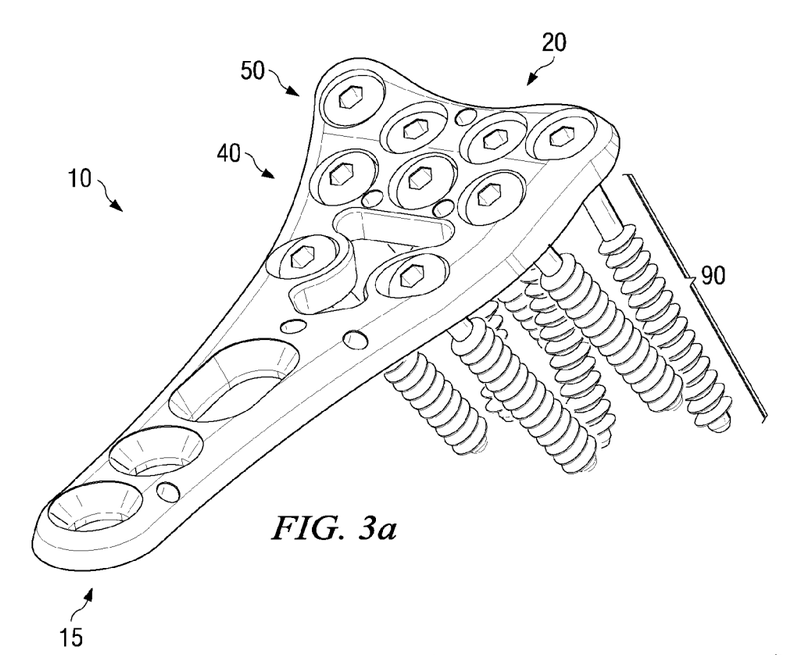
FIG. 3A is a perspective view of an embodiment of the volar plate, showing the bone screws used to affix the plate to the bone fragments inserted into the distal head of the volar plate.
Figure 3B:
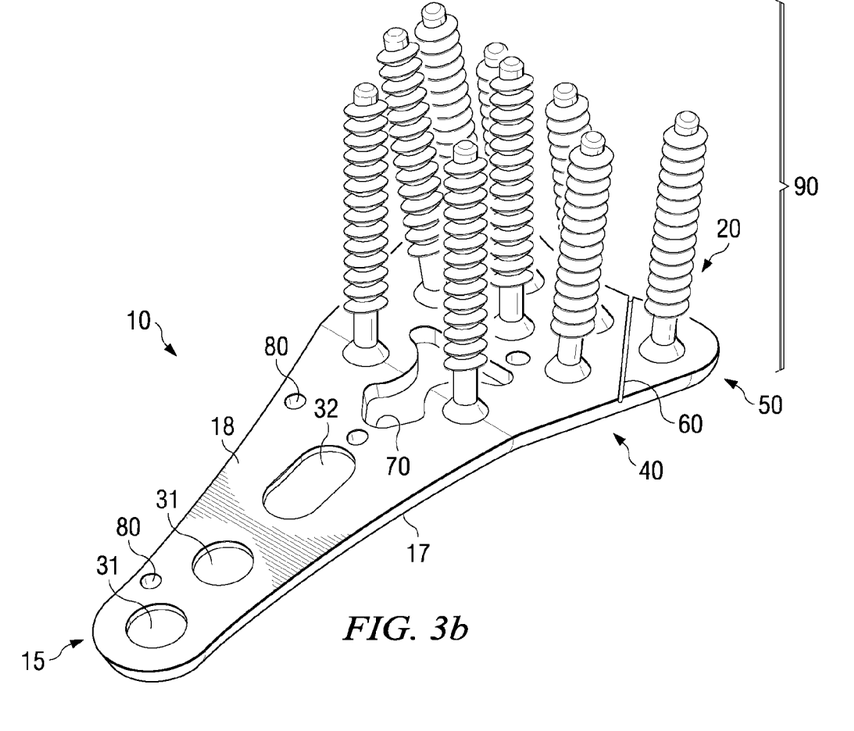
FIG. 3B is a second perspective view of an embodiment of the volar plate, rotated to show the underside of the plate.
Figure 3C:
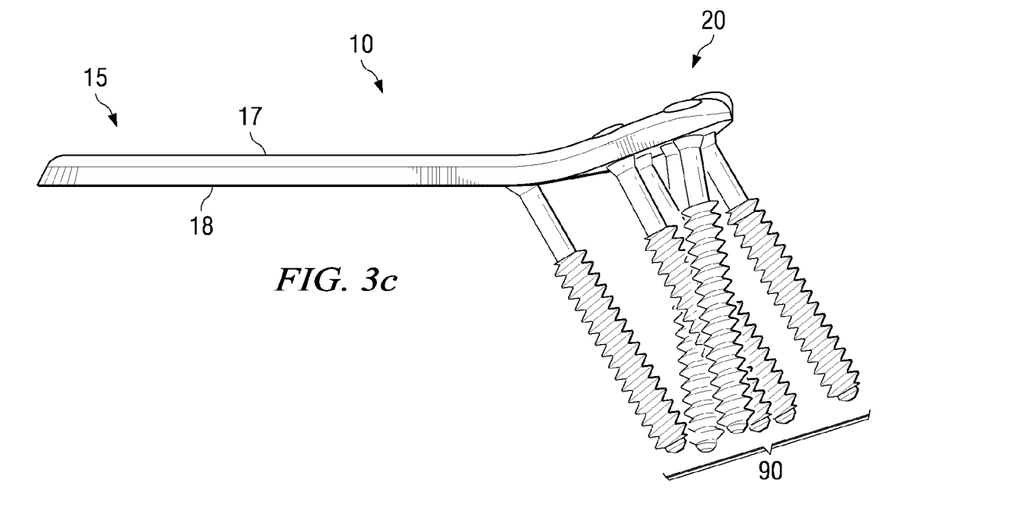
FIG. 3C is a side view of an embodiment of the volar plate, with bone screws in place in the distal head of the volar plate.

The distal head 20 of the volar plate 10 for FIG. 1 contains a plurality of threaded holes, through which bone screws (or some other fixation means) may be inserted to fix bone fragments in place relative to one another (as shown in FIG. 3C). While the volar plate 10 provides the underlying support, forming a steady base for affixing bone fragments, the bone screws 90 that screw into the threaded holes in the distal head 20 actually create the stabilization framework for the fracture. Generally, there are two rows of threaded screw holes located on the distal head 20 of the volar plate 10, and each of the holes are substantially the same size.

Each row of screw holes shown in FIG. 1 employs a substantially non-linear arrangement of holes, in an attempt to better match the contours of the wrist anatomy. The proximal row 40 of the volar plate 10 in FIG. 1 has three threaded bone screw holes 41, 42, and 43 countersunk into the upper surface 17 of the volar plate 10. The volar plate 10 of FIG. 1 utilizes a substantially non-linear alignment of the holes 41, 42, 43 in the proximal row 40, with the interior screw hole 42 distal to the two outside screw holes 41 and 43. Thus, in the embodiment of FIG. 1 the holes of proximal row 40 are staggered to essentially form a non-linear arc. In the specific exemplary embodiment shown in FIG. 1, the non-linear arc of the holes of the proximal row 40 proceeds from a proximal position, to a distal position, and back to a proximal position (generally forming a substantially parabolic arc). Alternatively, the proximal row 40 could form a non-linear arc that proceeds from a distal position, to a proximal position, and back to a distal position.

Distal row 50 of FIG. 1 has four threaded screw holes countersunk into the upper surface 17 of the volar plate 10. Again, the holes of the distal row 50 are arranged in a staggered, substantially non-linear alignment in an attempt to more closely match the contours of the distal radius, basically following the subchondral bone contour line in order to provide a stabilization framework that accommodates and interacts with the actual anatomy of the patient's wrist. So in the specific exemplary embodiment shown in FIG. 1, the interior holes 52 and 53 of the distal row 50 of screw holes would be located proximal to the two outer screw holes 51 and 54, such that the holes of distal row 50 essentially form a non-linear (often parabolic-shaped) arc curving in the opposite direction of the arc of proximal row 40. In other words, distal row 50 curves from a distal position to a proximal position, and back to a distal position in the embodiment of FIG. 1. Alternatively, the holes of the distal row 50 could form a non-linear arc curving from a proximal position, to a distal position, and back to a proximal position. The non-linear orientation of the holes of the proximal and distal rows allows for a more organic design that may better interact with the underlying bone structure, such that the screws may track anatomical features and offer superior support.

The orientation of the screw holes (based on the angle at which the holes penetrate the volar plate 10 and the angle at which the threads are set in the holes) determines the orientation of the bone screws 90 projecting out from the bottom surface of the head 20 of the volar plate 10. FIGS. 3A, 3B, 3C, and 3D illustrate one embodiment of the volar plate 10 with the bone screws 90 in place (screwed into the threaded holes in the volar plate 10), showing the projection of the shafts of the bone screws 90 out the bottom surface 18 of the head 20 of the volar plate 10. When the bone screws 90 are inserted into the screw holes (41, 42, 43, 51, 52, 53, and 54) in the head 20 of the volar plate 10 (by being screwed into the upper surface 17 of the volar plate 10 and projecting out from the bottom surface 18 of the volar plate 10), the distal row 50 of bone screws 90 would follow an angular orientation similar to the wrist joint surface, allowing the screws 90 to reach and obtain purchase in subchondral bone without entering the joint space, while the proximal row 40 of bone screws 90 would substantially converge on the distal row 50 of screws 90 to provide support while also possibly allowing the use of various screw lengths to accommodate various radius sizes, as necessary. Thus, the axes of the holes of the proximal row would substantially converge on the axes of the holes of the distal row, as both axes extend outward from the bottom surface of the volar plate. The term "converge" is intended here to describe the bone screws of the proximal row angling toward but not necessarily meeting or crossing the bone screws of the distal row in at least one plane.

In other words, the screws 90 of the proximal row 40 would generally extend out between the screws 90 of the distal row 50. Thus, the screws 90 of the distal and proximal rows would typically be interleaved, creating an effective stabilization framework for bone fragments. Such an alignment would allow for bone fragments to be engaged by bone screws 90 from multiple directions, so that the bone screws 90 might essentially cradle each bone fragment and provide an improved stabilization framework for supporting the fracture site. It also might allow multiple smaller fragments to be properly positioned, since a multitude of support axes would be available. And it might allow screws of various sizes to be used, such that longer screws typically required for larger radius sizes would not interfere with each other.

Figure 3D:
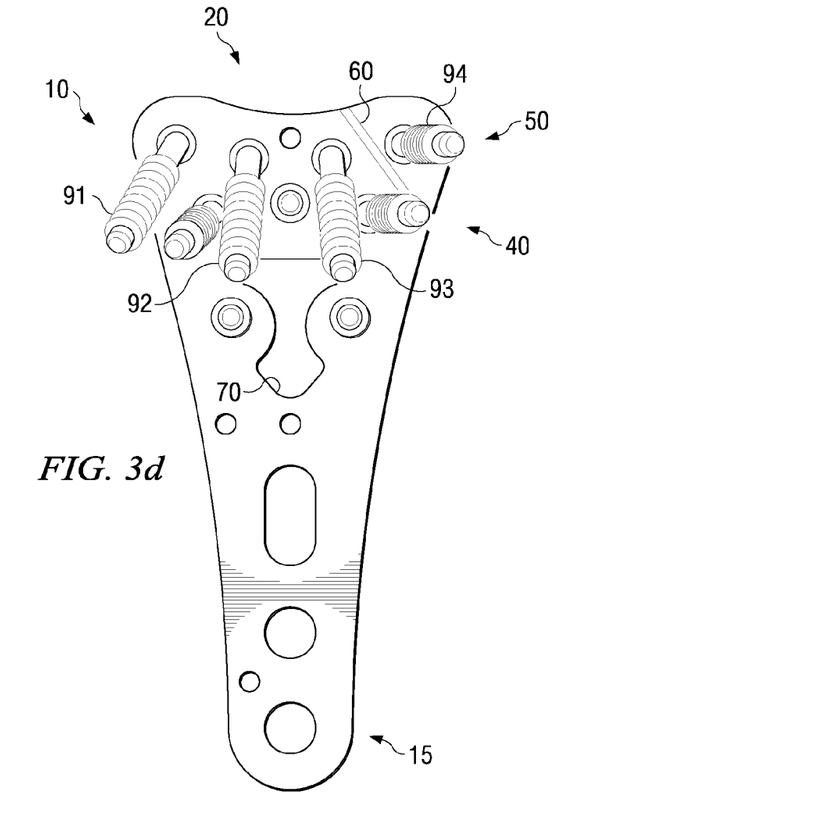
FIG. 3D is a plan view of the underside of an embodiment of the volar plate, showing the bottom surface of the volar plate with bone screws in place to illustrate the configuration and orientation of the bone screws with respect to one another.

The bone screw 90 alignment of FIG. 3D provides a detailed example. In the embodiment of FIG. 3D (as also shown in FIGS. 3A, 3B, and 3C), screws 90 in the distal row 50 project outward from the bottom surface 18 at an angle that can vary from substantially perpendicular to tilting towards the proximal end as they extend outward. In addition, the screws 90 may angle laterally as well. The outside screw 91 of the distal row 50 angles towards the proximal end of the volar plate 10, and may also simultaneously angle out away from the volar plate 10 laterally. The inside screw 92 (of the distal row) next to outside screw 91 angles towards the proximal end to a greater degree than does outside screw 91. The other inside screw 93 angles towards the proximal end less than both inside screw 92 and outside screw 91. The radial styloid screw 94 (which is the other outside screw corresponding to the corner of the head 20 of the volar plate 10 with a crease 60) is adjustable based on the position to which the corner is bent when fitting the volar plate 10 to the specific anatomical structure of the patient. The radial styloid screw 94 projects out to be substantially perpendicular to the bottom surface 18 of that corner of the head 20 of the volar plate 10. Since the corner of the head 20 of the volar plate 10 with the radial styloid 94 is typically flexed upward (such that the upper surface 17 of that corner is concave), the radial styloid screw 94 generally angles outward, allowing greater purchase of the typically larger radial styloid fragment.

In the embodiment shown in FIG. 3D, each of the bone screws 90 of the distal row 50 tend to angle towards the proximal end within a range of angles from approximately six degrees to thirty-two degrees from normal. In addition, each of the screws 90 of the distal row 50 may angle laterally (in either lateral direction) within a range of angles between approximately zero degrees and ten degrees (as measured from a vertical center plane). These ranges are merely exemplary, however; any number of bone screw 90 angles may be appropriate, and all are intended to be included within the scope of the disclosure.

The screws 90 of the proximal row 40 in FIG. 3D each angle towards the distal end of the volar plate 10 as they extend outward, so that they converge on the screws 90 of the distal row 50. So as FIG. 3D illustrates, each of the seven threaded screw holes of the volar plate head 20 in this embodiment would generally be oriented so that the bone screws 90 inserted through them would project out in different directions, generally interleaving as the two rows converge. This provides for an effective stabilization framework, as bone fragments can be precisely held in the appropriate position in a manner that works with the underlying anatomical geometry of the distal radius. The precise bone screw placement described above for FIG. 3D may vary, and different embodiments may use alternative placements. The general goal when placing bone screws 90 through a volar plate 10 is to provide an effective stabilization framework for fixing the bone fragments in proper alignment, preferably taking into account the anatomical geometry of the region.

The volar plate 10 of the described embodiments also may contain a central cavity 70, located generally in the vicinity of the region of the volar plate 10 where the distal head 20 angles away from the proximal body 15. By way of example, FIG. 1 illustrates a central cavity 70. The central cavity 70 may promote bone growth by providing convenient access to proximal fracture sites for introduction of bone graft or bone void filler materials if needed during the treatment regimen. Furthermore, a plurality of mounting screw holes are located within the proximal body 15 of the volar plate 10, allowing for the plate to be mounted in place securely on the bone. Generally, the mounting screws would extend through the mounting screw holes substantially perpendicular to the bottom surface 18 of the body 15 of the volar plate. One or more mounting screw holes 31 are located towards the proximal end of the volar plate 10 (and one of these mounting screw holes could be configured as an elongated oval or slot 32, as shown in FIG. 1, allowing longitudinal movement of the volar plate 10 with respect to the shaft of the mounting screws for adjustment as the volar plate 10 is being affixed by the surgeon). These mounting screw holes allow the volar plate 10 to be firmly fixed in place on the bone using bone screws, providing a secure foundation for the stabilization framework. And in FIG. 1, two additional mounting screw holes 33 are distal to the proximal mounting screw holes 31 and the longitudinal slot 32, with one additional mounting screw hole 33 on either side of the central opening 70.

These additional (distal) mounting screw holes 33 may provide for a more secure attachment of the volar plate 10 to the patient's bone and/or allow fixation and support of more proximal fractures. Because of the placement of the two additional (distal) mounting screw holes 33 about the central cavity 70, the central cavity 70 of FIG. 1 is shaped to accommodate the screw placement by having a somewhat hourglass shape with a thinner waist in its middle. And given their distal position, it may be possible to utilize the additional (distal) mounting screws 33 to provide further support to the fracture site, in addition to possibly serving as additional mounting locations for secure attachment of the volar plate 10 to the bone. In this way, the distal mounting screw holes 33 may allow the volar plate 10 to address a wider range of fracture locations.

It should be noted that in the embodiment of FIG. 1, all of the bone screw holes in the distal head 20, as well as the two distal mounting screws 33, are threaded. Utilizing threaded holes allows the bone screws 90 to be securely fastened to the volar plate 10, such that they may then hold bone fragments in position with respect to the volar plate 10. Thus, locking screws tend to be used in the distal head 20. Mounting holes 31 (and the longitudinal slot 32) are not threaded in FIG. 1, since the mounting screws do not need to attach (with engaging threads) to the volar plate 10, but can simply hold the volar plate 10 in position against the bone. Thus, non-locking screws tend to be used in the body. Furthermore, all of the holes for the bone screws used with the volar plate 10 are countersunk in the embodiment shown in FIG. 1. While this is not essential, it does provide a smoother upper surface 17, resulting in less irritation to the area surrounding the volar plate 10. And bone screws, with threading substantially along the length of their shafts, seem to provide a more secure stabilization framework, since they obtain purchase in the bone fragments.

In the disclosed embodiment of FIG. 3C, locking bone screws 90 are generally used within the distal head 20. The additional distal mounting screws (used within holes 33) may be either locking or non-locking, while the mounting screws (used within holes 31 and 32) tend to be non-locking. In the embodiment of FIG. 3C, screws generally range from approximately 6 mm to 28 mm in length (depending upon the specific fracture situation). The diameter of the locking screws generally ranges from approximately 2 mm to 2.7 mm, while the non-locking screws (used for mounting the volar plate 10 to the bone) tend to be approximately 3.5 mm in diameter. These screw dimensions are only exemplary, however; a wide range of screws may be appropriate given the specific situation, and all are intended to be included within the scope of this disclosure.

Finally, the volar plate 10 may include smaller holes for K-wires 80, allowing temporary fixation of the volar plate 10 in place during the surgical procedure in such a way that the surgeon may correctly position and temporarily fix the volar plate 10 prior to affixing it securely to the bone via bone screws. A plurality of K-wire holes 80 are positioned generally along the volar plate 10 in such a way as to allow for effective temporary placement of the volar plate during the mounting procedure.

In practice, the volar plate 10 would be mounted directly to the volar surface of the distal radius bone during a surgical operation for aligning and fixing bone fragments of a wrist fracture. By anatomically aligning the volar plate 10 within the pronator quadratus fossa, the bone screws may obtain purchase in the dorsal subchondral bone without danger of protrusion into the joint. The bottom face 18 of the volar plate 10 would be placed in contact with the bone, with the surgeon positioning the volar plate 10 as needed. Typically, the distal head portion 20 of the volar plate 10 would be placed over the bone fragments, so that bone screws 90 may be used to fix the position of the bone fragments.

Generally, K-wires would be inserted through the guide holes 80 to temporarily fix the volar plate 10 onto the bone during the procedure and/or to provide an approximation of the projected axis of an adjacent screw position prior to actual insertion of the screw. The K-wires may also allow the surgeon to verify the approximate placement and angle that a screw may take in the bone. Since several of the K-wire holes 80 of the disclosed embodiment generally mimic the angle of nearby screw holes, the surgeon may preliminarily verify correct placement by examining the K-wire attachment to the bone via x-ray prior to drilling bone screw holes. The surgeon may then drill holes into the bone for the bone screws to enter and engage the bone.

Figure 4:
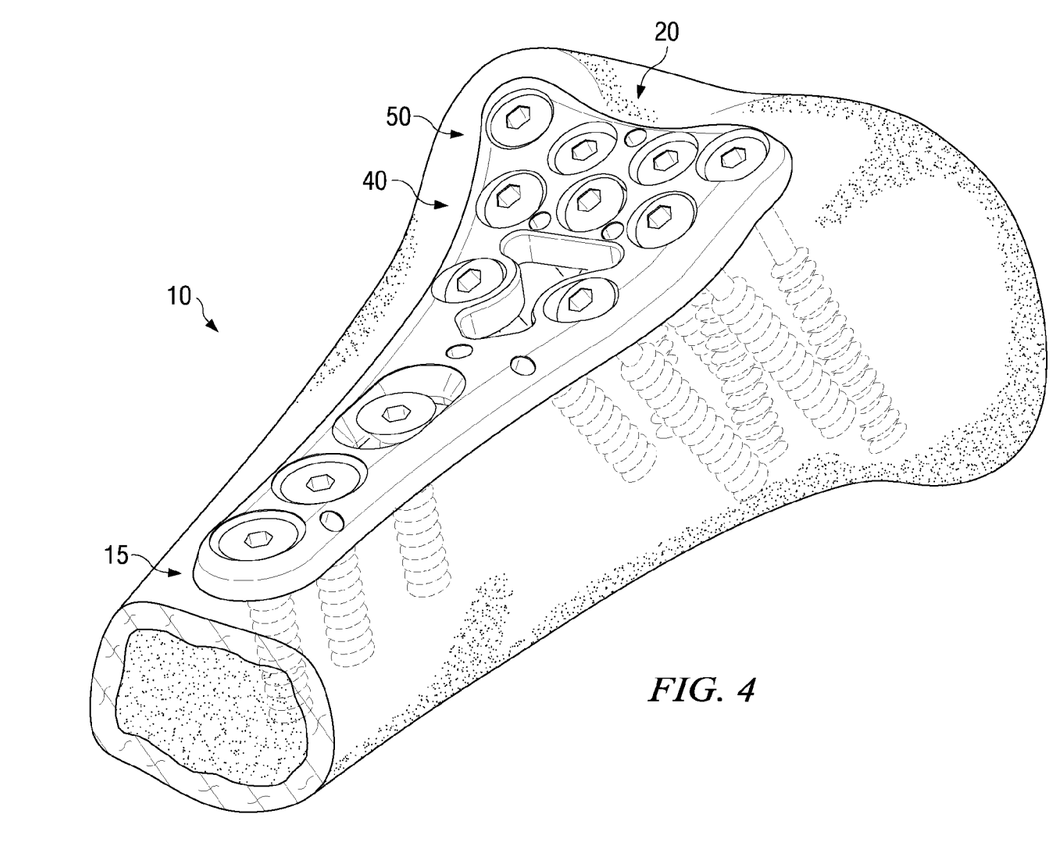
FIG. 4 is an illustrative perspective view of an exemplary volar plate held in place upon a distal volar radius bone in the wrist using a plurality of bone screws.

For the exemplary embodiment of FIG. 1, once the volar plate 10 has been roughly positioned using K-wires, a bone screw would be inserted into the longitudinal slot 32 and loosely tightened in place on the bone. The volar plate 10 would then be finally positioned (with adjustments being made longitudinally as needed by sliding the plate position based upon the location of the screw within the slot), and the bone screw in slot 32 would be tightened. The bone fragments would then generally be properly aligned, and bone screws 90 would be utilized to fix the position of the bone fragments. Finally, the remaining mounting screws would be inserted through holes 31, firmly fixing the volar plate 10 in place on the bone. FIG. 4 illustrates an exemplary volar plate 10 fixed in position with respect to the volar surface of the distal radius bone, with bone screws securing the volar plate and fixing the position of bone fragments.

Figure 5:
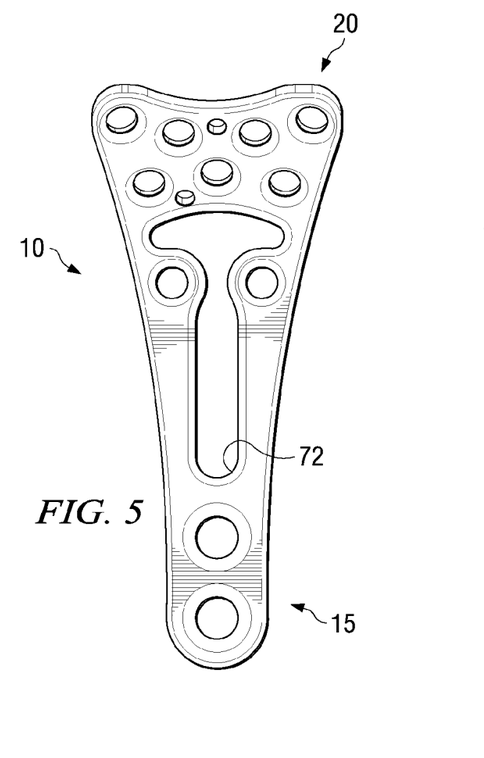
FIG. 5 is a plan view of an alternative embodiment of the volar plate, wherein the central cavity and the longitudinal screw slot have been joined.
Figure 6:
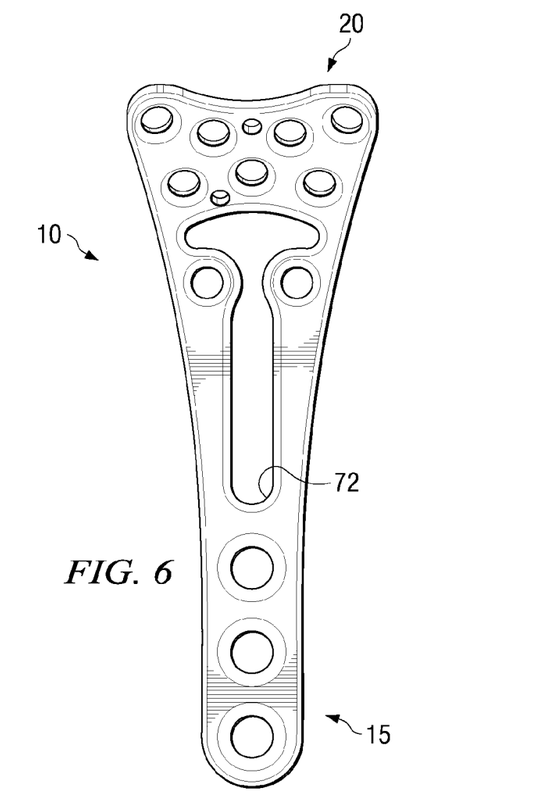
FIG. 6 is a plan view of an alternative embodiment of the volar plate having an elongated proximal body portion.
Figure 7:
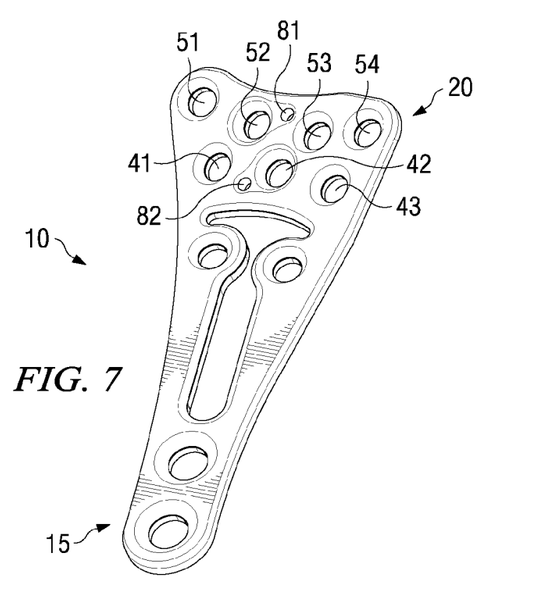
FIG. 7 is an illustrative perspective view showing a volar plate of the type shown in FIG. 3A in which each of the K-wire holes of the distal head have axes substantially parallel to that of a corresponding bone screw hole and are visually linked with their corresponding bone screw holes.

FIGS. 5, 6, and 7 illustrate alternative embodiments of the volar plate 10. FIG. 5, for example, employs a central cavity 72, wherein the basic central cavity 70 of FIG. 1 would be physically linked with the longitudinal mounting slot 32 of FIG. 1 to form an elongated central cavity 72. This embodiment would allow maximum advantage from the central cavity 72, while also enhancing longitudinal adjustment capabilities. FIG. 6 is similar, but the proximal body 15 is extended longitudinally, providing a longer volar plate 10 that can also accommodate shaft fractures.

FIG. 7 illustrates an embodiment in which the K-wire holes in the distal head 20 of the volar plate 10 are visually linked with their associated, corresponding bone screw holes. As described above, each of the seven threaded bone screw holes in the distal head 20 of this embodiment of the volar plate 10 project outward in different directions. It may be helpful for proper mounting if several of the K-wire holes in the distal head 20 would project outward in the same general direction as specific corresponding bone screw holes, such that the center-line axis of each K-wire hole in the distal head would be substantially parallel to the center-line axis of the corresponding bone screw hole. This type of orientation would aid the surgeon in properly aligning bone fragments with K-wires prior to final fixation with bone screws.

In order to be most effective, however, the surgeon should be able to easily determine which K-wire hole is associated with a particular bone screw hole. By visually linking each K-wire hole to its corresponding bone screw hole in the distal head 20 of the volar plate 10, the surgeon would be able to simply identify which bone screw hole relates to a particular K-wire hole. By way of example, a geometrical marking (such as forming both the K-wire hole and the bone screw hole within the same indented area) or a graphical linking (such as a laser marking or a color coordinated marking system) could be used as the means for visually linking associated K-wire holes and bone screw holes. The example of FIG. 7 illustrates an embodiment of the volar plate 10 in which K-wire hole 81 is visually linked with bone screw hole 52, while K-wire hole 82 is visually linked with bone screw hole 42.

While various embodiments in accordance with the principles disclosed herein have been described above, it should be understood that they have been presented by way of example only, and not limitation. Thus, the breadth and scope of the invention(s) should not be limited by any of the above-described exemplary embodiments, but should be defined only in accordance with any claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of the Invention," the claims should not be limited by the language chosen under this heading to describe the so-called field. Further, a description of a technology in the "Background of the Invention" is not to be construed as an admission that certain technology is prior art to any invention(s) in this disclosure. Neither is the "Brief Summary of the Invention" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What we claim is:

1. A volar plate comprising:
    a substantially flat proximal body; and
    a distal head coupled to the proximal body;
    wherein:
        the distal head is wider than the proximal body;
        the distal head angles upward away from the plane of the proximal body, forming a substantially concave upper surface;
        the distal head comprises a plurality of threaded holes formed therethrough;
        the plurality of threaded holes are arranged in at least two rows, with a proximal row of at least three holes and a distal row of at least three holes;
        the threaded holes of the proximal row are arranged nonlinearly, and the threaded holes of the distal row are arranged nonlinearly;
        the distal row includes one or more interior threaded holes and two outside threaded holes, the one or more interior holes being proximal to the two outside holes;
        the holes of the distal row are all located more distal from the proximal body than all of the holes of the proximal row; and
        the proximal row of threaded holes forms a substantially parabolic arc, with the location of the holes of the proximal row proceeding from a proximal position, to a distal position, to a proximal position.

2. A volar plate as in claim 1, further comprising one or more K-wire holes in the distal head of the volar plate, wherein:
    each K-wire hole corresponds to one of the plurality of threaded holes in the distal head of the volar plate, with the center-line axis of each K-wire hole substantially parallel to the center-line axis of its corresponding threaded hole in the distal head; and
    each K-wire hole is correlated to its corresponding threaded hole in the distal head by a geometrical marking in the surface of the volar plate.

3. A volar plate as in claim 1 further comprising a central cavity that extends from the distal end of the proximal body into the proximal end of the distal head.

4. A volar plate as in claim 3 further comprising two mounting screw holes, wherein one mounting screw hole is located laterally on either side of the central cavity.

5. A volar plate as in claim 1, wherein the proximal row includes one or more interior threaded holes and two outside threaded holes, the one or more interior holes being distal to the two outside holes.

6. A volar plate as in claim 1, wherein the distal row of threaded holes forms a substantially non-linear arc, with the location of the holes of the distal row proceeding from a distal position, to a proximal position, to a distal position.

7. A volar plate as in claim 6, wherein the proximal row includes one or more interior threaded holes and two outside threaded holes, the one or more interior holes of the proximal row being distal to the two outside holes of the proximal row.

8. A volar plate as in claim 7 further comprising a bottom surface, wherein the plurality of threaded holes in the distal head of the volar plate are oriented so that the axes of the holes in the distal row project outward from the bottom surface angling proximally within a range of angles from approximately 6 to 32 degrees from normal, and the axes of the holes in the proximal row project outward from the bottom surface and substantially converge on the axes of the holes of the distal row as both axes project outward from the bottom surface of the volar plate.

9. A volar plate as in claim 7, wherein the volar plate is substantially Y-shaped.

10. A volar plate as in claim 7 further comprising one or more K-wire holes in the distal head of the volar plate, wherein:
    each K-wire hole corresponds to one of the plurality of threaded holes in the distal head of the volar plate, with the center-line axis of each K-wire hole substantially parallel to the center-line axis of its corresponding threaded hole in the distal head; and
    each K-wire hole is correlated to its corresponding threaded hole in the distal head by a geometrical marking in the surface of the volar plate.

11. A volar plate as in claim 7 further comprising a central cavity that extends from the distal end of the proximal body into the proximal end of the distal head.

12. A volar plate as in claim 11 further comprising two mounting screw holes, wherein one mounting screw hole is located laterally on either side of the central cavity.

13. A volar plate as in claim 12, wherein the two mounting screw holes are threaded.

14. A volar plate comprising:
    a substantially flat proximal body;
    a distal head coupled to the proximal body; and
    a plurality of bone screws with threaded shafts;
    wherein:
        the distal head is wider than the proximal body and tapers to the narrower proximal body;
        the distal head angles upward away from the plane of the proximal body, forming a substantially concave upper surface;
        the distal head comprises a plurality of threaded holes;
        the plurality of threaded holes are arranged in two rows that cross a longitudinal axis of the plate, with a proximal row of at least three holes and a distal row of at least three holes;
        the holes of the proximal row and the holes of the distal row are arranged non-linearly, wherein the displacement of the holes with respect to each other is measured along the longitudinal axis of the plate;
        the distal row includes one or more interior threaded holes and two outside threaded holes, the one or more interior holes being proximal to the two outside holes;

the holes of the distal row are all located more distal from the proximal body than all of the holes of the proximal row;

the plurality of bone screws penetrate and threadably engage the distal head through the plurality of threaded holes, such that the shafts of the bone screws project outward away from the bottom surface of the volar plate; and the proximal row of threaded holes forms a substantially parabolic arc, with the location of the holes of the proximal row proceeding from a proximal position, to a distal position, to a proximal position.

15. A volar plate as in claim 14, wherein:

the proximal row includes one or more interior threaded holes and two outside threaded holes, the one or more interior holes being distal to the two outside holes; and the distal row includes one or more interior threaded holes and two outside threaded holes, the one or more interior holes being proximal to the two outside holes, and wherein the distal row of threaded holes forms a substantially parabolic arc, with the location of the holes of the distal row proceeding from a distal position, to a proximal position, to a distal position.

16. A volar plate as in claim 14, wherein the volar plate is substantially Y-shaped.

17. A volar plate as in claim 14 further comprising a central cavity that extends from the distal end of the proximal body into the proximal end of the distal head.

18. A volar plate as in claim 17 further comprising two mounting screw holes, wherein one mounting screw hole is located laterally on either side of the central cavity.

19. A volar plate as in claim 18, wherein the volar plate is substantially Y-shaped.

20. A volar plate as in claim 19, wherein:

the proximal row includes one or more interior threaded holes and two outside threaded holes, the one or more interior holes being distal to the two outside holes; and the distal row of threaded holes forms a substantially parabolic arc, with the location of the holes of the distal row proceeding from a distal position, to a proximal position, to a distal position.

21. A volar plate as in claim 20, wherein:

the bottom surface of the volar plate is operable to be placed in contact with a radius bone's volar surface proximal to a wrist joint; and the plurality of threaded holes in the distal head of the volar plate are oriented so that the shafts of the bone screws projecting out from the holes of the distal row extend out away from the bottom surface of the volar plate and are generally aligned with the joint surface so as to obtain purchase in the bone's subchondral layer, and the shafts of the bone screws projecting out from the holes of the proximal row substantially converge on the shafts of the bone screws from the distal row.

22. A volar plate as in claim 21 further comprising one or more K-wire holes in the distal head of the volar plate, wherein:

each K-wire hole corresponds to one of the plurality of threaded holes in the distal head of the volar plate, with the center-line axis of each K-wire hole substantially parallel to the center-line axis of its corresponding threaded hole in the distal head; and each K-wire hole is correlated to its corresponding threaded hole in the distal head by a geometrical marking in the surface of the volar plate.

23. A fixation device comprising a volar plate having a wider distal end tapering to a substantially flat, narrower proximal end, wherein:

the distal end angles upward away from the plane of the proximal end, forming a substantially concave upper surface at the distal end of the volar plate;

the distal end comprises a plurality of threaded holes;

the plurality of threaded holes are arranged in two rows that cross a longitudinal axis of the plate, with a proximal row of at least three holes and a distal row of at least four holes;

the holes of the proximal row and the holes of the distal row are arranged nonlinearly, wherein the displacement of the holes with respect to each other is measured along the longitudinal axis of the plate;

the distal row includes two or more interior threaded holes and two outside threaded holes, the two or more interior holes being proximal to the two outside holes;

the holes of the distal row are all located more distal from the proximal body than all of the holes of the proximal row; and the proximal row of threaded holes forms a substantially parabolic arc, with the location of the holes of the proximal row proceeding from a proximal position, to a distal position, to a proximal position.

24. A fixation device as in claim 23, wherein the distal row of threaded holes curves to substantially track the subchondral bone contour line of a distal radius bone.

25. A fixation device as in claim 24, wherein the proximal row includes one or more interior threaded holes and two outside threaded holes, the one or more interior holes being distal to the two outside holes.

26. A fixation device as in claim 25 further comprising a central cavity, wherein the central cavity is disposed proximal to the plurality of threaded holes in the distal end, substantially in the vicinity where the distal end angles away from the plane of the proximal end.

27. A fixation device as in claim 26 further comprising two threaded mounting screw holes, wherein one mounting screw hole is located laterally on either side of the central cavity.

28. A fixation device as in claim 27, wherein the volar plate is substantially Y-shaped.

29. A fixation device as in claim 28 further comprising one or more K-wire holes in the distal end of the volar plate, wherein:

each K-wire hole corresponds to one of the plurality of threaded holes in the distal end of the volar plate, with the center-line axis of each K-wire hole substantially parallel to the center-line axis of its corresponding threaded hole in the distal end; and each K-wire hole is correlated to its corresponding threaded hole in the distal end of the volar plate by a geometrical marking in the surface of the volar plate.

30. A fixation device as in claim 28 further comprising a plurality of bone screws with threaded shafts, wherein:

the volar plate comprises a bottom surface operable to be placed in contact with a radius bone's volar surface proximal to a wrist joint;

the plurality of bone screws penetrate and threadably engage the volar plate through the plurality of threaded holes, such that the shafts of the bone screws project outward away from the bottom surface of the volar plate; and the plurality of holes in the distal head of the volar plate are oriented so that the shafts of the bone screws projecting out from the holes of the distal row extend out away from the bottom surface of the volar plate and are generally aligned with the joint surface so as to be operable to obtain purchase in the bone's subchondral layer, and the shafts of the bone screws projecting out from the holes of the proximal row substantially converge on the shafts of the bone screws from the distal row.

31. A volar plate as in claim 1, further comprising one or more K-wire holes in the distal head of the volar plate, wherein:
- each K-wire hole corresponds to one of the plurality of threaded holes in the distal head of the volar plate, with the center-line axis of each K-wire hole substantially parallel to the center-line axis of its corresponding threaded hole in the distal head; and
- each K-wire hole is correlated to its corresponding threaded hole in the distal head by a graphical link in the surface of the volar plate.

32. A volar plate as in claim 7 further comprising one or more K-wire holes in the distal head of the volar plate, wherein:
- each K-wire hole corresponds to one of the plurality of threaded holes in the distal head of the volar plate, with the center-line axis of each K-wire hole substantially parallel to the center-line axis of its corresponding threaded hole in the distal head; and
- each K-wire hole is correlated to its corresponding threaded hole in the distal head by a graphical link in the surface of the volar plate.

33. A volar plate as in claim 14, wherein the proximal and distal rows of threaded holes are transverse to a longitudinal axis of the volar plate and the non-linear arrangement of the rows is defined by the displacement of each threaded hole along the longitudinal axis of the volar plate.

34. A volar plate as in claim 21 further comprising one or more K-wire holes in the distal head of the volar plate, wherein:
- each K-wire hole corresponds to one of the plurality of threaded holes in the distal head of the volar plate, with the center-line axis of each K-wire hole substantially parallel to the center-line axis of its corresponding threaded hole in the distal head; and
- each K-wire hole is correlated to its corresponding threaded hole in the distal head by a graphical link in the surface of the volar plate.

35. A volar plate as in claim 23, wherein the proximal and distal rows of threaded holes are transverse to a longitudinal axis of the volar plate and the non-linear arrangement of the rows is defined by the displacement of each threaded hole along the longitudinal axis of the volar plate.

36. A fixation device as in claim 28 further comprising one or more K-wire holes in the distal end of the volar plate, wherein:
- each K-wire hole corresponds to one of the plurality of threaded holes in the distal end of the volar plate, with the center-line axis of each K-wire hole substantially parallel to the center- line axis of its corresponding threaded hole in the distal end; and
- each K-wire hole is correlated to its corresponding threaded hole in the distal end of the volar plate by a graphical link in the surface of the volar plate.

37. A volar plate as in claim 1, wherein the distal head comprises a crease along the bottom surface of one outside corner.

38. A volar plate as in claim 14, wherein the distal head comprises a crease along the bottom surface of one outside corner.

39. A fixation device as in claim 23, wherein the distal head comprises a crease along the bottom surface of one outside corner.

* * * * *